United States Patent [19]

Franz et al.

[11] 4,226,611

[45] Oct. 7, 1980

[54] N-PHOSPHONOMETHYLGLYCINE THIOESTER HERBICIDES

[75] Inventors: John E. Franz, Crestwood; Robert J. Kaufman, University City, both of Mo.

[73] Assignee: Monsanto Company, St. Louis, Mo.

[21] Appl. No.: 957,394

[22] Filed: Nov. 3, 1978

[51] Int. Cl.³ ................... A01N 57/12; A01N 57/14; C07F 9/40
[52] U.S. Cl. ..................................... 71/87; 260/941
[58] Field of Search ................. 260/941; 71/87, 86

[56] References Cited

U.S. PATENT DOCUMENTS

| | | | |
|---|---|---|---|
| 3,799,758 | 3/1974 | Franz | 71/86 |
| 3,991,095 | 11/1976 | Gaertner | 71/87 |
| 4,120,689 | 10/1978 | Dutra | 71/86 |

*Primary Examiner*—Catherine L. Mills
*Attorney, Agent, or Firm*—William T. Black; Donald W. Peterson

[57] ABSTRACT

This disclosure relates to a new class of organic chemical compounds. More particularly, this disclosure is concerned with novel thioester derivatives of N-phosphonomethylglycine wherein alkylthio or substituted alkylthio groups are bonded to the phosphorus atom. This class of compounds has been found to display desirable herbicidal activity when applied to certain varieties of weeds or undesired plants.

30 Claims, No Drawings

N-PHOSPHONOMETHYLGLYCINE THIOESTER HERBICIDES

This invention relates to a new class of organic chemical compounds. More particularly, this invention is concerned with novel thioester derivatives of N-phosphonomethylglycine wherein alkylthio or substituted alkylthio groups are bonded to the phosphorus atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

U.S. patent application Ser. No. 922,900 filed July 10, 1978 describes certain thioester derivatives of N-trifluoroacetyl-N-phosphonomethylglycine.

The compounds of the present invention are represented by the formula

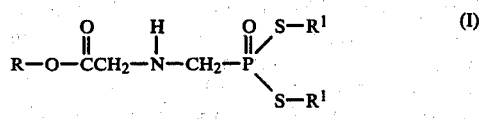

wherein R is a member of the class consisting of alkyl of from 1 to 6 carbon atoms, chloroalkyl of from 1 to 4 carbon atoms and alkoxyalkyl groups and each $R^1$ is a member of the class consisting of alkenyl of from 2 to 4 carbon atoms, alkyl containing from 1 to 6 carbon atoms, phenylalkyl wherein the alkyl group contains up to 4 carbon atoms, and mixtures thereof. It is preferred that R be alkyl of from 1 to 5 carbon atoms and even more preferred that R represent ethyl or methyl. It is preferred that $R^1$ represents alkenyl, alkyl of from 1 to 6 carbon atoms or phenylalkyl wherein the alkyl group contains up to 4 carbon atoms. It is even more preferred that $R^1$ be alkyl containing from 1 to 5 carbon atoms.

Illustrative of the alkyl groups represented by R and $R^1$ are methyl, ethyl, n- and isopropyl, n-, sec-, iso- and tert-butyl, pentyl and hexyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like. The phenylalkyl groups represented by $R^1$ include phenylmethyl, phenylethyl, phenylpropyl and phenylbutyl.

In accordance with the present invention, the compounds are prepared by reacting a compound of the formula

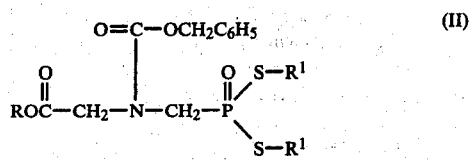

wherein R and $R^1$ are as above defined with hydrogen bromide in glacial acetic acid at a temperature of from $-10°$ C. to $+20°$ C. and then treating the resultant product with propylene oxide in an aprotic solvent. Preferably, the temperature is maintained at approximately 0° C.

The solvent that can be employed to produce the compounds of this invention for obvious reasons should be anhydrous to prevent hydrolysis of the thioester.

The starting materials for the production of the compounds of this invention are prepared by the following procedure which for simplicity employs ethyl N-phosphonomethylglycine as the reagent.

Ethyl N-phosphonomethylglycine (9.85 g., 0.05 mole) and benzyl chloroformate (9.4 g., 0.05 mole) were dissolved in 50 ml. of water and sodium carbonate (7.95 g., 0.075 mole) was added over a ½ hour period. The solution was stirred until all of the benzyl chloroformate had reacted. Concentrated hydrochloric acid (12.5 ml) was then added. Upon standing ethyl N-carbobenzoxy-N-phosphonomethylglycinate separated as an oil. The oil was then dried in a vacuum dessicator over phosphorus pentoxide at 0.55 torr. A 4 g. sample of the oil was dissolved in oxalyl chloride (20 ml) and stirred until gas evolution ceased. The mixture was concentrated in vacuo to yield ethyl N-carbobenzoxy-N-(dichlorophosphonomethyl)glycinate as a colorless oil. The oil is treated with an excess of oxalyl chloride to convert it to ethyl N-carbobenzoxy-N-phosphonomethylglycine dichloride which is then reacted with the appropriate thiol of the formula $R^1SH$ wherein $R^1$ is as above defined, in the presence of a tertiary amine hydrogen halide acceptor such as triethylamine. The product is recovered by chromatography on a silica gel column employing methylene chloride and/or diethyl ether as eluants. Other ester derivative starting materials for use in the production of the compounds of this invention are prepared by the same procedure employing the appropriate ester of N-phosphonomethylglycine.

The following examples serve to further illustrate this invention. In the examples all parts are parts by weight unless otherwise expressly set forth.

EXAMPLE 1

Ethyl N-carbobenzoxy-N-(dimethylthiophosphinylmethyl)glycine (2 g., 0.005 mole) was dissolved in 36% hydrogen bromide (8 ml) in glacial acetic acid at 0° C. and the resulting mixture was stirred for one hour. Ether was added and the oily precipitate was isolated by decanting the ether layer. The oil was washed with ether twice, then suspended in benzene and treated with propylene oxide. The solution was concentrated in vacuo to yield ethyl N-(dimethylthiophosphinylmethyl)glycine (0.7 g., 0.002 mole) as an amber oil, $N_D^{22} = 1.4832$.

EXAMPLE 2

Ethyl N-carbobenzoxy-N-(diisopropylthiophosphinylmethyl)glycine (2 g., 0.0044 mole) was reacted with 36% hydrogen bromide (8 ml) in glacial acetic acid. Ether was added and the oily precipitate was isolated by decanting the ether layer. The oil was washed with ether twice, then suspended in benzene and treated with propylene oxide. The solution was concentrated in vacuo to yield ethyl N-(diisopropylthiophosphinylmethyl)glycine (0.7 g., 0.0022 mole) as an oil, $N_D^{22} = 1.5066$.

EXAMPLE 3

Ethyl N-carbobenzoxy-N-(dibutylthiophosphinylmethyl)-glycine (2 g., 0.0046 mole) was reacted with 36% hydrogen bromide (10 ml) in glacial acetic acid at 0° C. Ether was added and the oily precipitate was isolated by decanting the ether layer. The oil was washed with ether twice, then suspended in benzene and treated with propylene oxide. The solution was concentrated in vacuo to yield ethyl N-(dibutylthiophosphinylmethyl)glycine as an amber oil, $N_D^{22} = 1.4820$.

EXAMPLE 4

Ethyl N-carbobenzoxy-N-(diethylthiophosphinylmethyl)glycine (1 g., 0.0024 mole) was dissolved in 5 ml. of 30% hydrogen bromide in glacial acetic acid at 0° C. The mixture was stirred for one hour. Ether was added and the oily precipitate was isolated by decanting the ether layer. The oil was washed with ether twice, then suspended in benzene and treated with propylene oxide. The solution was concentrated in vacuo to yield ethyl N-(diethylthiophosphinylmethyl)glycine (0.15 g., 0.0005 mole) as an oil, $N_D^{25} = 1.4960$.

EXAMPLE 5

Ethyl N-carbobenzoxy-N-(di-sec-butylthiophosphinylmethyl)glycine (1 g., 0.0023 mole) was dissolved in 5 ml. of 30% hydrogen bromide in glacial acetic acid at 0° C. The mixture was stirred for one hour. Ether was added and the oily precipitate isolated by decanting the ether layer. The oil was washed twice with ether and then suspended in benzene and treated with propylene oxide. The solution was concentrated in vacuo to yield ethyl N-(di-sec-butylthiophosphinylmethyl)-glycine (0.04 g., 0.001 mole) as an oil, $N_D^{25} = 1.3450$.

EXAMPLE 6

Ethyl N-carbobenzoxy-N-(diisobutylthiophosphinylmethyl)glycine (4 g., 0.009 mole) was dissolved in 10 ml. of 35% hydrogen bromide in glacial acetic acid at 0° C. The mixture was stirred for one hour. Ether was added and the oily precipitate isolated by decanting the ether layer. The oil was washed twice with diethyl ether and then suspended in benzene and treated with propylene oxide. The solution was concentrated in vacuo to yield ethyl N-(diisobutylthiophosphinylmethyl)glycine (0.3 g., 0.001 mole) as an oil, $N_D^{25} = 1.5121$.

EXAMPLE 7

β-chloroethyl N-carbobenzoxy-N-(diethylthiophosphinylmethyl)glycine (10.4 g., 0.023 mole) was reacted with 25 ml. of 32% hydrogen bromide in acetic acid at 0° C. The mixture was stirred for one hour. Diethyl ether was added and the oily precipitate isolated by decanting the ether layer. The oil was washed twice with diethyl ether and then suspended in benzene. The suspension was treated with propylene oxide. The resulting solution was concentrated in vacuo to yield β-chloroethyl N-(diethylthiophosphinylmethyl)glycine (1.5 g., 0.005 mole) as an oil, $N_D^{25} = 1.5310$.

EXAMPLE 8

β-chloroethyl N-carbobenzoxy-N-(dibenzylthiophosphinylmethyl)glycine (7.5 g., 0.013 mole) was reacted with 30% hydrogen bromide (20 ml) in glacial acetic acid at 0° C. The mixture was stirred for one hour. Diethyl ether was added and the oily precipitate isolated by decanting the ether layer. The oil was washed twice with diethyl ether, suspended in benzene and treated with propylene oxide. The resulting solution was concentrated in vacuo to yield β-chloroethyl N-(dibenzylthiophosphinylmethyl)glycine as an oil, $N_D^{22} = 1.5564$.

EXAMPLE 9 n-Butyl N-carbobenzoxy-N-[bis(3-phenylpropylthio)-phosphinylmethyl]glycine (9.0 g., 0.014 mole) was reacted with 32% hydrogen bromide (20 ml) in acetic acid at 0° C. Diethyl ether was added and the oily precipitate isolated by decanting the ether layer. The oil was washed twice with ether, suspended in benzene and then treated with propylene oxide. The resulting solution was concentrated in vacuo to yield n-butyl N-[bis(3-phenylpropylthio)phosphinylmethyl]glycine (0.8 g., 0.002 mole) as an oil, $N_D^{22} = 1.5253$.

EXAMPLE 10 n-Butyl N-carbobenzoxy-N-[bis(pentylthio)phosphinylmethyl]glycine (5.5 g., 0.01 mole) was reacted with 32% hydrogen bromide (15 ml) in glacial acetic acid at 0° C. Diethyl ether was added and the oily precipitate isolated by decantation of the ether layer. The oil was washed twice with ether, suspended in benzene and then treated with propylene oxide. The resulting solution was concentrated in vacuo to yield n-butyl N-[bis(pentylthio)phosphinylmethyl]-glycine (0.7 g., 0.002 mole) as an oil, $N_D^{27} = 1.4905$.

EXAMPLE 11

Ethoxyethyl N-carbobenzoxy-N-[bis(allylthio)phosphinylmethyl]glycine (4.8 g., 0.01 mole) was reacted with 32% hydrogen bromide (15 ml) in glacial acetic acid at 0° C. Ether was added and the oily precipitate was isolated by decanting the ether layer. The oil was washed with ether twice, then suspended in benzene and treated with propylene oxide. Concentration of the solution in vacuo yielded ethoxyethyl N-[bis(allylthio)-phosphinylmethyl]glycine as an oil, $N_D^{22} = 1.5163$.

EXAMPLE 12

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

Table I

| Compound of Example No. | WAT | kg/h | A | B | C | D | E | F | G | H | I | J | K |
|---|---|---|---|---|---|---|---|---|---|---|---|---|---|
| 1* | 4 | 11.2 | 3 | 4 | 4 | 3 | 3 | 4 | 3 | 4 | 4 | 4 | 4 |
| 1* | 4 | 5.6 | 2 | 3 | 4 | 3 | 4 | 4 | 3 | 4 | 4 | 4 | 4 |
| 2* | 4 | 11.2 | 4 | 4 | 4 | 4 | 4 | 4 | 4 | 4 | 4 | 4 | 4 |
| 2* | 4 | 5.6 | 4 | 3 | 4 | 3 | 4 | 4 | 4 | 4 | 3 | 4 | 4 |
| 3* | 4 | 11.2 | 1 | 2 | 1 | 1 | 4 | 3 | 2 | 4 | 4 | 3 | 4 |
| 3* | 4 | 5.6 | 3 | 4 | 2 | 1 | 4 | 4 | 3 | 4 | 4 | 3 | 4 |
| 4* | 4 | 11.2 | 4 | 3 | 4 | 3 | 4 | 4 | 4 | 4 | 4 | 4 | 4 |
| 4* | 4 | 5.6 | 4 | 4 | 4 | 3 | 4 | 4 | 3 | 3 | 4 | 4 | 4 |
| 5* | 4 | 11.2 | 4 | 4 | 3 | 2 | 4 | 4 | 3 | 3 | 4 | 4 | 4 |
| 5* | 4 | 5.6 | 4 | 3 | 3 | 2 | 4 | 4 | 2 | 2 | 2 | 4 | 4 |
| 6* | 4 | 11.2 | 3 | 4 | 4 | 4 | 4 | 4 | 4 | 4 | 4 | 4 | 4 |
| 6* | 4 | 5.6 | 2 | 4 | 3 | 3 | 4 | 4 | 2 | 4 | 3 | 2 | 3 |
| 7 | 4 | 11.2 | 3 | 4 | 4 | 3 | 4 | 4 | 4 | 4 | 4 | 4 | 4 |
| 7 | 4 | 5.6 | 3 | 4 | 3 | 3 | 3 | 4 | 4 | 4 | 4 | 2 | 4 |
| 8 | 4 | 11.2 | 4 | 4 | 3 | 3 | 3 | 4 | 3 | 3 | 4 | 3 | 4 |
| 8 | 4 | 5.6 | 2 | 3 | 3 | 2 | 3 | 4 | 3 | 3 | 4 | 3 | 3 |
| 9 | 4 | 11.2 | 2 | 4 | 4 | 2 | 1 | 4 | 2 | 3 | 3 | 3 | 4 |
| 9 | 4 | 5.6 | 2 | 3 | 1 | 2 | 1 | 4 | 2 | 4 | 3 | 1 | 4 |
| 10 | 4 | 11.2 | 2 | 3 | 4 | 2 | 1 | 4 | 2 | 4 | 4 | 2 | 4 |
| 10 | 2 | 5.6 | 1 | 3 | 1 | 1 | 1 | 3 | 1 | 1 | 1 | 1 | 3 |
| 11 | 4 | 11.2 | 3 | 4 | 4 | 2 | 3 | 4 | 3 | 3 | 4 | 4 | 4 |
| 11 | 4 | 5.6 | 4 | 3 | 4 | 3 | 3 | 4 | 3 | 4 | 4 | 4 | 4 |

*Formulated just prior to spraying in tetrahydrofuran.

Table II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1* | 4 | 5.6 | 4 | 4 | 4 | 4 | 4 | 3 | 3 | 4 | 4 | 3 | 4 | 4 | 3 | | | |
| 1* | 4 | 1.12 | 1 | 4 | 4 | 4 | 3 | 2 | 2 | 3 | 3 | 4 | 3 | 4 | 4 | 3 | 4 | |
| 1* | 4 | 0.28 | 1 | 3 | 3 | 2 | 3 | 2 | 2 | 2 | 2 | 3 | 2 | 1 | 2 | 3 | 2 | 3 |
| 1* | 4 | 0.056 | 1 | 1 | 0 | 0 | 1 | 1 | 0 | 0 | 0 | 1 | 1 | 0 | 0 | 1 | 1 | 2 |
| 2 | 4 | 5.6 | 2 | 4 | 4 | 4 | 4 | 3 | 4 | 3 | 4 | 4 | 4 | 4 | 4 | 4 | 4 | 4 |
| 2 | 4 | 1.12 | 1 | 2 | 3 | 3 | 4 | 2 | 2 | 2 | 1 | 4 | 4 | 4 | 3 | 4 | 3 | 4 |
| 2 | 4 | 0.28 | 1 | 1 | 1 | 1 | 2 | 1 | 1 | 1 | 1 | 3 | 2 | 1 | 1 | 2 | 2 | 3 |
| 3 | 4 | 5.6 | 2 | 3 | 4 | 2 | 4 | 4 | 4 | 3 | 2 | 4 | 4 | 3 | 4 | 3 | 3 | 4 |
| 3 | 4 | 1.12 | 1 | 2 | 1 | 1 | 2 | 2 | 2 | 2 | 1 | 2 | 1 | 2 | 2 | 3 | 3 | 3 |
| 3 | 4 | 0.28 | 1 | 0 | 0 | 0 | 2 | 2 | 1 | 1 | 1 | 2 | 2 | 1 | 1 | 2 | 1 | 2 |
| 3 | 2 | 0.056 | 0 | 0 | 0 | 0 | 0 | 1 | 1 | 1 | 0 | 0 | 0 | 0 | 0 | 0 | 0 | 1 |
| 4 | 4 | 5.6 | 4 | 4 | 4 | 4 | 4 | 4 | 4 | 4 | 4 | 4 | 4 | 4 | 4 | 4 | 4 | 4 |
| 4 | 4 | 1.12 | 2 | 4 | 3 | 3 | 3 | 3 | 2 | 2 | 3 | 4 | 4 | 3 | 4 | 4 | 4 | 4 |
| 4 | 4 | 0.28 | 1 | 2 | 2 | 2 | 3 | 2 | 1 | 2 | 2 | 4 | 4 | 2 | 2 | 4 | 2 | 3 |
| 4 | 2 | 0.056 | 1 | 0 | 1 | 1 | 1 | 1 | 0 | 1 | 0 | 1 | 1 | 0 | 0 | 1 | 1 | 1 |
| 5 | 4 | 5.6 | 3 | 4 | 4 | 4 | 4 | 3 | 2 | 4 | 3 | 4 | 4 | 4 | 4 | 4 | 4 | 4 |
| 5 | 4 | 1.12 | 1 | 4 | 4 | 3 | 3 | 3 | 3 | 2 | 2 | 4 | 4 | 4 | 4 | 4 | 3 | 4 |
| 5 | 4 | 0.28 | 1 | 2 | 2 | 0 | 3 | 2 | 1 | 2 | 2 | 4 | 4 | 1 | 2 | 3 | 3 | 4 |
| 5 | 4 | 0.056 | 1 | 1 | 1 | 0 | 1 | 1 | 1 | 1 | 0 | 2 | 2 | 0 | 1 | 1 | 2 | 2 |
| 6 | 4 | 5.6 | 4 | 4 | 4 | 4 | 4 | 3 | 3 | 4 | 4 | 4 | 4 | 4 | 4 | 4 | 4 | 4 |
| 6 | 4 | 1.12 | 3 | 4 | 4 | 3 | 4 | 1 | 3 | 4 | 4 | 4 | 4 | 3 | 4 | 3 | 4 | |
| 6 | 4 | 0.28 | 1 | 3 | 3 | 2 | 3 | 2 | 1 | 2 | 2 | 3 | 3 | 2 | 1 | 4 | 3 | 3 |
| 7 | 4 | 5.6 | 4 | 4 | 4 | 4 | 4 | 4 | 4 | 3 | 4 | 4 | 3 | 3 | 4 | 4 | 4 | 4 |

Table II-continued

| Compound of Example No. | WAT | kg h | Plant Species | | | | | | | | | | | | | | | |
|---|---|---|---|---|---|---|---|---|---|---|---|---|---|---|---|---|---|---|
| | | | L | M | N | O | P | B | Q | D | R | E | F | C | J | S | K | T |
| 7 | 4 | 1.12 | 4 | 4 | 3 | 3 | 4 | 4 | 4 | 3 | 2 | 4 | 4 | 4 | 4 | 4 | 4 | 4 |
| 8 | 4 | 5.6 | 2 | 4 | 4 | 3 | 3 | 2 | 2 | 2 | 1 | 3 | 4 | 3 | 2 | 4 | 4 | 4 |
| 8 | 4 | 1.12 | 1 | 3 | 2 | 2 | 4 | 2 | 1 | 2 | 0 | 1 | 3 | 1 | 0 | 4 | 3 | 3 |
| 9 | 4 | 5.6 | 4 | 4 | 4 | 4 | 4 | 4 | 4 | 3 | 4 | 4 | 4 | 3 | 3 | 4 | 4 | 4 |
| 9 | 4 | 1.12 | 1 | 4 | 4 | 1 | 3 | 4 | 4 | 2 | 1 | 4 | 4 | 2 | 3 | 4 | 4 | 4 |
| 9 | 4 | 0.28 | 0 | 3 | 1 | 0 | 3 | 1 | 1 | 1 | 0 | — | — | 1 | 1 | 2 | 2 | 4 |
| 10 | 4 | 5.6 | 3 | 4 | 4 | 4 | 4 | 4 | 4 | 3 | 4 | 4 | 4 | 4 | 4 | 4 | 4 | 4 |
| 10 | 4 | 1.12 | 2 | 4 | 4 | 1 | 4 | 3 | 4 | 2 | 2 | — | 4 | 2 | 3 | 4 | 4 | 4 |
| 10 | 4 | 0.28 | 0 | 1 | 3 | 0 | 3 | 1 | 4 | 2 | 0 | 1 | 2 | 1 | 0 | 2 | 3 | 3 |
| 11 | 4 | 5.6 | 4 | 4 | 4 | 4 | 4 | 4 | 4 | 3 | 4 | 4 | 4 | 4 | 4 | 4 | 4 | 4 |
| 11 | 4 | 1.12 | 1 | 4 | 4 | 3 | 3 | 2 | 1 | 2 | 2 | 4 | 4 | 1 | 4 | 4 | 3 | 4 |
| 11 | 4 | 0.28 | 0 | 0 | 1 | 0 | 1 | 1 | 1 | 1 | 1 | — | 1 | 0 | 0 | 3 | 2 | 3 |

*Formulated just prior to spraying in tetrahydrofuran.

EXAMPLE 13

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in the following table.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

Table III

| Compound of Example No. | WAT | kg h | Plant Species | | | | | | | | | |
|---|---|---|---|---|---|---|---|---|---|---|---|---|
| | | | A | B | C | D | E | F | G | H | I | J | K |
| 1 | 2 | 11.2 | 3 | 0 | 0 | 0 | 0 | 0 | 0 | 0 | 0 | 0 | 0 |
| 2 | 2 | 11.2 | 2 | 0 | 0 | 0 | 0 | 0 | 0 | 0 | 0 | 0 | 0 |
| 3 | 2 | 11.2 | 3 | 0 | 0 | 0 | 0 | 0 | 0 | 0 | 0 | 0 | 0 |
| 4 | 4 | 11.2 | 3 | 0 | 0 | 0 | 3 | 0 | 0 | 3 | 2 | 2 | 0 |
| 5 | 2 | 11.2 | 0 | 0 | 0 | 0 | 0 | 0 | 0 | 2 | 2 | 0 | 0 |
| 6 | 2 | 11.2 | 3 | 0 | 0 | 0 | 0 | 0 | 0 | 3 | 2 | 3 | 0 |
| 7 | 2 | 11.2 | 3 | 0 | 0 | 0 | 0 | 0 | 0 | 3 | 2 | 0 | 0 |
| 8 | 2 | 11.2 | 0 | 0 | 0 | 0 | 0 | 0 | 0 | 0 | 0 | 0 | 0 |
| 9 | 2 | 11.2 | 0 | 0 | 0 | 0 | 0 | 0 | 0 | 0 | 0 | 0 | 0 |
| 10 | 2 | 11.2 | 0 | 0 | 0 | 0 | 0 | 0 | 0 | 0 | 0 | 0 | 0 |
| 11 | 2 | 11.2 | 0 | 0 | 0 | 0 | 0 | 0 | 0 | 0 | 0 | 0 | — |

From the test results presented in Tables I and II, it can be seen that the post-emergent herbicidal activity of the compounds of this invention is, for the most part, general in nature. In certain specific instances, however, some selectivity is demonstrated. The pre-emergent test in Table III shows some selectivity. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent, one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 11.2 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

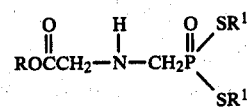

wherein R is a member of the class consisting of alkyl of from 1 to 6 carbon atoms, chloroalkyl of from 1 to 4 carbon atoms and alkoxyalkyl and each $R^1$ is a member of the class consisting of alkyl of from 1 to 6 carbon atoms, alkenyl of from 2 to 4 carbon atoms, phenylalkyl wherein the alkyl group contains of from 1 to 4 carbon atoms and mixtures thereof.

2. A compound of claim 1 wherein R is alkyl of from 1 to 6 carbon atoms.

3. A compound of claim 1 wherein R is chloroalkyl of from 1 to 4 carbon atoms.

4. A compound of claim 1 wherein R is ethoxyethyl.

5. A compound of claim 2 wherein $R^1$ is alkyl of from 1 to 6 carbon atoms.

6. A compound of claim 3 wherein $R^1$ is alkyl of from 1 to 6 carbon atoms.

7. A compound of claim 4 wherein $R^1$ is allyl.

8. A compound of claim 3 wherein $R^1$ is ethyl.

9. A compound of claim 5 wherein $R^1$ is methyl.

10. A compound of claim 5 wherein $R^1$ is ethyl.

11. A herbicidal composition comprising a herbicidally effective amount of a compound of claim 1 together with an inert diluent.

12. A herbicidal composition comprising a herbicidally effective amount of a compound of claim 2 together with an inert diluent.

13. A herbicidal composition comprising a herbicidally effective amount of a compound of claim 3 together with an inert diluent.

14. A herbicidal composition comprising a herbicidally effective amount of a compound of claim 4 together with an inert diluent.

15. A herbicidal composition comprising a herbicidally effective amount of a compound of claim 5 together with an inert diluent.

16. A herbicidal composition comprising a herbicidally effective amount of a compound of claim 6 together with an inert diluent.

17. A herbicidal composition comprising a herbicidally effective amount of a compound of claim 7 together with an inert diluent.

18. A herbicidal composition comprising a herbicidally effective amount of a compound of claim 8 together with an inert diluent.

19. A herbicidal composition comprising a herbicidally effective amount of a compound of claim 9 together with an inert diluent.

20. A herbicidal composition comprising a herbicidally effective amount of a compound of claim 10 together with an inert diluent.

21. A herbicidal method which comprises contacting a plant with a herbicidally effective amount of a compound of claim 1.

22. A herbicidal method which comprises contacting a plant with a herbicidally effective amount of a compound of claim 2.

23. A herbicidal method which comprises contacting a plant with a herbicidally effective amount of a compound of claim 3.

24. A herbicidal method which comprises contacting a plant with a herbicidally effective amount of a compound of claim 4.

25. A herbicidal method which comprises contacting a plant with a herbicidally effective amount of a compound of claim 5.

26. A herbicidal method which comprises contacting a plant with a herbicidally effective amount of a compound of claim 6.

27. A herbicidal method which comprises contacting a plant with a herbicidally effective amount of a compound of claim 7.

28. A herbicidal method which comprises contacting a plant with a herbicidally effective amount of a compound of claim 8.

29. A herbicidal method which comprises contacting a plant with a herbicidally effective amount of a compound of claim 9.

30. A herbicidal method which comprises contacting a plant with a herbicidally effective amount of a compound of claim 10.

* * * * *